United States Patent

Shinoda et al.

Patent Number: 5,304,205
Date of Patent: Apr. 19, 1994

[54] SURGICAL FILAMENT

[75] Inventors: Hosei Shinoda; Masami Ohtaguro; Shigeru Iimuro, all of Aichi, Japan

[73] Assignee: Mitsui Toatsu Chemicals, Incorporated, Tokyo, Japan

[21] Appl. No.: 840,200

[22] Filed: Feb. 24, 1992

Related U.S. Application Data

[63] Continuation-in-part of Ser. No. 625,899, Nov. 29, 1990, abandoned.

[30] Foreign Application Priority Data

Dec. 11, 1989 [JP] Japan .................................. 1-318822
Feb. 27, 1991 [JP] Japan .................................. 3-032839

[51] Int. Cl.$^5$ ........................ A61L 17/00; A61B 17/04
[52] U.S. Cl. ............................... 606/230; 606/228; 606/231; 427/2; 428/364; 428/375; 428/378; 428/392
[58] Field of Search ............... 606/228–231; 428/361, 364, 375, 378, 392, 395; 427/2

[56] References Cited

FOREIGN PATENT DOCUMENTS 2297051 8/1976 France .
60-25974 6/1985 Japan .
61-76163 4/1986 Japan .

Primary Examiner—C. Fred Rosenbaum
Assistant Examiner—Ronald K. Stright, Jr.
Attorney, Agent, or Firm—Burns, Doane, Swecker & Mathis

[57] ABSTRACT

A surgical filament which has a surface coated with at least one N-long chain monoacylated basic amino acid having an aliphatic acyl group of from 6 to 22 carbon atoms or with a composition containing at least one of said N-long chain monoacylated basic amino acid, and has improved surface-slipping characteristics such as the ability to be passed through tissue and tie down property.

12 Claims, 2 Drawing Sheets

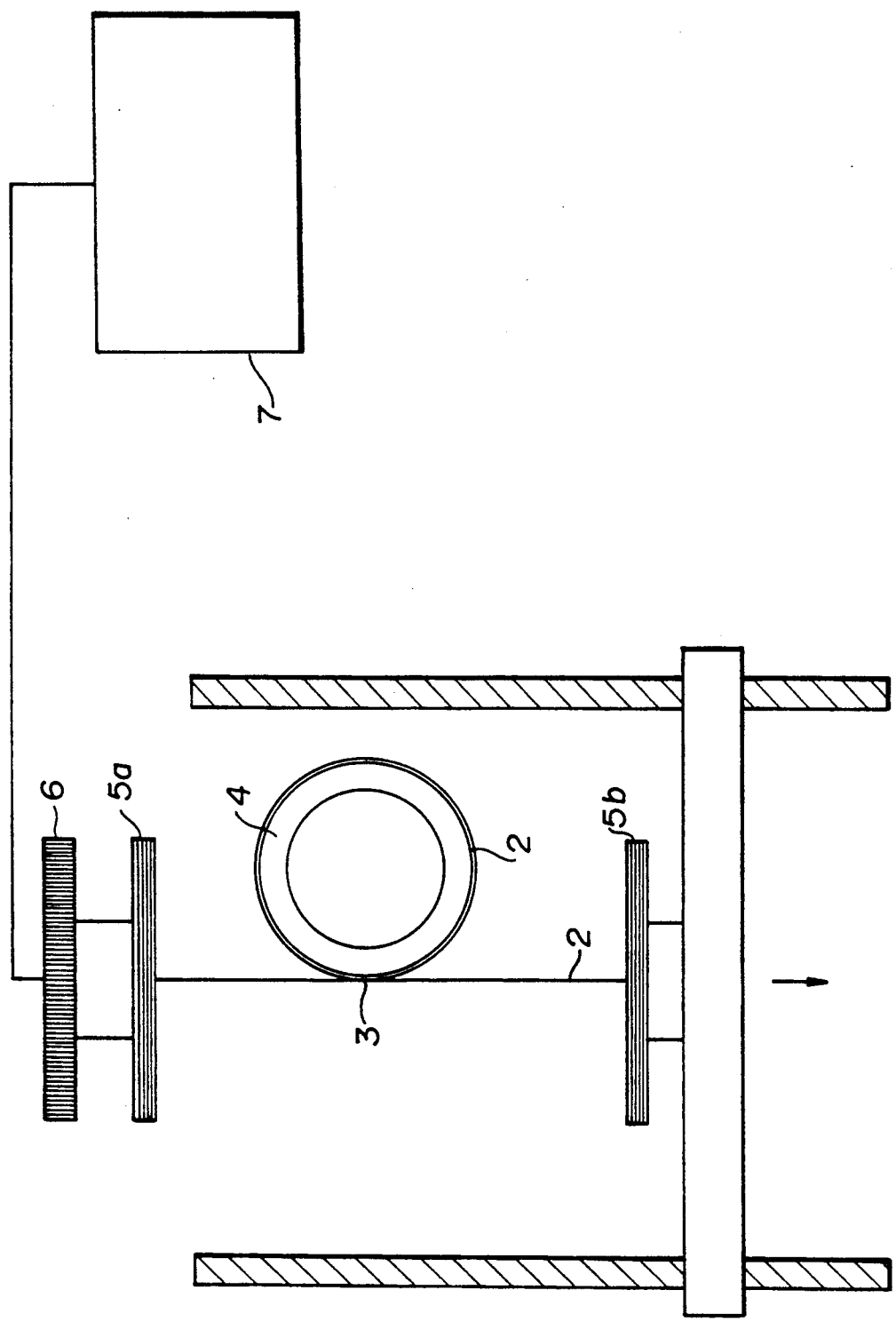

SURGICAL FILAMENT

CROSS REFERENCE TO RELATED APPLICATION

This is a continuation-in-part of our application Ser. No. 07/625,899 filed on Nov. 29, 1990 now abandoned.

BACKGROUND OF THE INVENTION

1. Field of the Invention

The present invention relates to a surgical filament such as a surgical suture or ligature having improved surface-slipping characteristics, for example, having the ability to pass through the tissue and be tied.

2. Description of the Related Art

Various surgical filament's such as sutures and ligatures are used in surgery for the suturing, fixation and ligation of tissues including the internal organs, skin, muscles, bones, joints and blood vessels.

These surgical filaments are sometimes used for sutures and ligatures in the form of a monofilament. However, these filaments are often used in the form of multifilament or as a braided or twisted structure.

Even in the case of a monofilament having relatively good surface-slipping characteristics, untreated surfaces of the monofilament often exhibit insufficient smoothness. Consequently, tissue is sometimes damaged in the course of suturing or fixation by non-negligible friction between the filament and tissue. In order to prevent such trouble or to slide a knot of the suture to a desired position, various coatings are applied to the surgical filaments.

For example, Japanese Patent Publication SHO 60-25974(1985) discloses a synthetic multifilament suture covered with a mixture composed of a metal salt of a higher fatty acid and a bioabsorbable polymer. Japanese Laid-Open Patent SHO 61-76163(1986) describes a surgical filament dry-coated with a metal salt of a higher fatty acid.

The surgical filaments are, in the course of surgery, usually exposed to body fluids or passed through wet tissue from once to several times before making a knot.

When a conventionally known coating agent, for example, calcium stearate is coated on a bioabsorbable suture, a certain extent of the lubricating effect can be observed in the dry state. On the other hand, the surface-slipping characteristics are sometimes impaired in the wet state and thus it becomes difficult to slide a knot of the suture to the desired position. Additionally, there is a problem that passing the filament through the tissue is unsatisfactory.

BRIEF DESCRIPTION OF THE DRAWINGS

FIG. 2 is a drawing illustrating a schematic view of the equipment used for the tie down test. In the drawings, 1 is a section of a bar, 2 is a filament, 2a and 2b are both ends of the filament, 3 is a knot, 4 is a sponge, 5a and 5b are chucks of a tensile tester, 6 is a load cell and 7 is a recorder.

SUMMARY OF THE INVENTION

Figure 1:
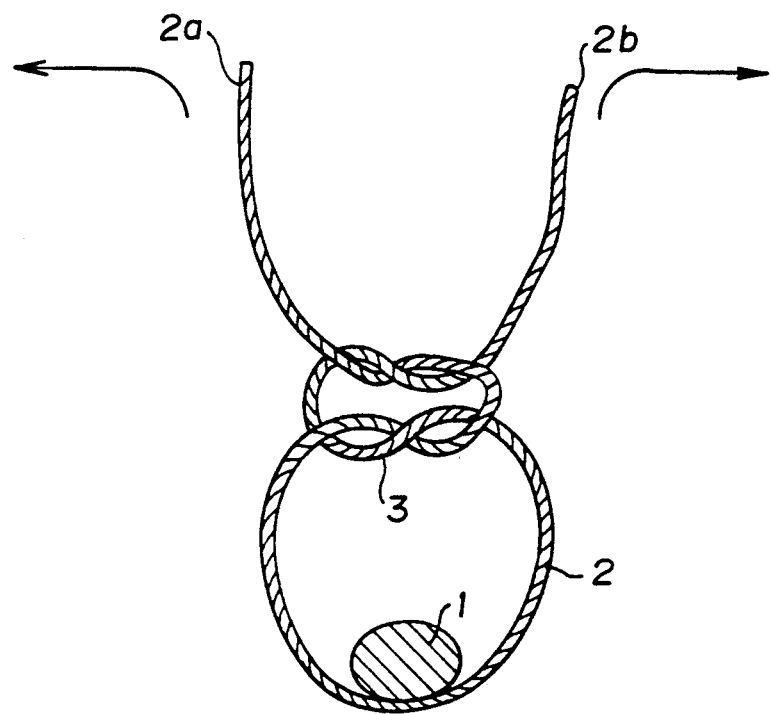
FIG. 1 is a drawing illustrating a manner of tying a filament specimen and the tensile direction in the tie down test.

An object of the present invention is to provide a surgical filament having improved surface-slipping characteristics by use of a specific coating agent. A more particular object is to provide a surgical filament having surface-slipping characteristics such as tie down property and the ability to be passed through tissue in the wet state substantially equal to those characteristic in the dry state and also having a high safety for the organism.

Another object of the present invention is to solve the above problems and to provide a process for the preparation of a surgical filament which has good appearance and which retains the coating agent during packaging, transportation, storage and use as a suture or a ligature.

A further object of the present invention is to provide a process for preparing a surgical filament which can maintain surface-slipping characteristics substantially constant in both wet and dry states though coated with a small amount of the coating agent and which has a high safety for the organism.

As a result of carrying out an intensive investigation to accomplish the above objects, the present inventors have found that a surgical filament having excellent surface-slipping characteristics such as outstanding tie down property and the ability to be passed through tissue in the wet state can be obtained by coating the surgical filament with a basic amino acid having a long chain acyl group. Thus the present invention has been completed.

Accordingly, one aspect of the present invention is a surgical filament comprising a surface coated with at least one N-long chain monoacylated basic amino acid which has an aliphatic acyl group of from 6 to 22 carbon atoms or with a composition containing at least one of said N-long chain monoacylated basic amino acid, and having improved surface-slipping characteristics.

The application of at least one N-long chain monoacylated basic amino acid or a composition containing the amino acid to the surface of the surgical filament is carried out by a method for directly attaching the powder of the amino acid to the surface of the surgical filament without solvent, or a method for passing the filament through a suspension of the amino acid in a solvent and successively removing the solvent to yield a dry coated filament, or a method for adhering the amino acid to the surface of the filament in the form of a composition containing the amino acid and a bioabsorbable and thermoplastic or solvent-soluble polymer. The amount of the N-long chain monoacylated basic amino acid is from 0.1 to 20 parts by weight per 100 parts by weight of the filament.

As a result of further investigation, the present inventors have found that it is effective for solving the above problems to coat on the surface of a surgical filament N-long chain monoacylated basic amino acid having a specific particle size.

The N-long chain monoacylated basic amino acid is in the form of white flaky crystals having an average particle size of 20 to 30 $\mu$m and a maximum particle size of about 100 $\mu$m. When the N-long chain monoacylated basic amino acid is attached to the surface of the surgical filament, large particles of the amino acid are adhered intact.

When powder containing a large particle size of at least one N-long chain monoacylated basic amino acid or the amino acid composition is directly attached to the surface of the filament without using a solvent, or when the powder of the composition containing the amino acid is dispersed in a molten, thermoplastic, bioabsorbable polymer and adhered to the surface of the filament, the amount required to coat the surface is at least 20% by weight based on the weight of the filament in order to obtain a satisfactory surface-slipping property. A coating amount exceeding 10% by weight or application of the powder containing a large particle size of the N-long chain monoacylated basic amino acid leads to reduction of the commodity value because the surface of the filament looks like a wheat flour coated surface and becomes pale white.

Further, the N-long chain monoacylated basic amino acid having a large particle size has a small area of adhesion per unit weight and is hence liable to have a low adhesive force.

Consequently, when the surgical filament coated with the N-long chain monoacylated basic amino acid is packaged, transported, stored or used as a suture or a ligature, the powder of N-long chain monoacylated basic amino acid falls off and contaminates the surroundings or the surface-slipping characteristics of the filament such as tie down property and the ability to be passed through the tissue are substantially decreased.

When a knot is made in a surgical filament or tied down to the suture area in a practical operation of surgical suture, the powder of N-long chain monoacylated basic amino acid falls off by friction and substantially decreases the surface-slipping characteristics. Further, released powder unfavorably scatters over the diseased part of a human body and it is required to wash and remove the powder.

Consequently, another aspect of the present invention is a preparation process of a surgical filament comprising coating the surface of the surgical filament by using a coating material selected from the group consisting of (1) the powder of at least one N-long chain monoacylated basic amino acid having an aliphatic acyl group of from 6 to 22 carbon atoms wherein 80% by volume or more of particles has a size of 20 μm or less, (2) a suspension of said powder, and (3) a composition containing said powder.

The present invention is more preferably a preparation process for a surgical suture comprising coating a surgical filament with said N-long chain monoacylated basic amino acid which has a volume percentage of 80% or more on particles having a size of 20 μm or less and additionally has an average particle size of 7 μm or less.

The N-long chain monoacylated basic amino acid which has an aliphatic acyl group of from 6 to 22 carbon atoms and is preferably used in the surgical filament is a compound represented by the formula (I):

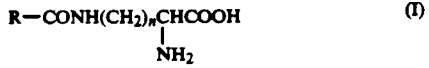

wherein R is a long chain alkyl group having from 5 to 21 carbon atoms and n is an integer of from 1 to 4.

The N-long chain monoacylated basic amino acid used in the invention may be coated singly on the filament or may be used as a component of a coating composition composed of several components. In the composition containing at least one of the N-long chain monoacylated basic amino acid, bioabsorbable polymers are preferably used as other components. The bioabsorbable polymers include, for example, polyglycolic acid, polylactic acid and a copolymer of glycolic acid and lactic acid which are polymers of glycolide and/or lactide The raw material of the filament is preferably composed of bioabsorbable polymers which include, for example, polyglycolic acid, polylactic acid, glycolide-lactide copolymers, and additionally glycolide-caprolactone copolymers, polyhydroxy-butyric acid, poly-p-dioxanone and trimethylene carbonate polymers.

The surgical filament of the invention may be coated with the N-long chain monoacylated basic amino acid having an aliphatic acyl group of from 6 to 22 carbon atoms neat. As an alternative method, at least one of the N-long chain monoacylated basic amino acid having an aliphatic acyl group of from 6 to 22 carbon atoms or an admixture thereof with other bioabsorbable polymers is dissolved or suspended in water or a volatile solvent. The surgical filament is dipped into the liquid thus obtained and coated so as to obtain a coat weight of from 0.1 to 20 parts by weight per 100 parts by weight of the filament. Successively the solvent is removed to obtain a coated filament.

The process of preparing the filament of the invention provides a surgical filament which can maintain the surface-slipping characteristics such as tie down property and the ability to be passed through the tissue substantially constant in both wet and dry states and has a high safety for the organism.

That is, the surgical filament prepared by the process of the invention has good appearance and retains the coating agent during packaging, transportation, storage and use as a suture or a ligature. Further, good slipping characteristics can be provided for the surgical filament with a smaller amount of coating. These effects can be remarkably observed in particular when the surgical filament has a braided structure.

When the term "coating" is used in the invention, coating is not necessarily required to cover the whole surface of the filament. A mottled covering or spotted adhesion of the coating agent may also be partially found on the filament surface.

DESCRIPTION OF THE PREFERRED EMBODIMENTS

The N-long chain monoacylated basic amino acid used in the invention has a structure of an amino group in a basic amino acid having a plurality of amino groups is acylated with a long chain carboxylic acid.

In such N-long chain monoacylated basic amino acid, the basic amino acid includes, for example, α,β-diaminopropionic acid, α,γ-diaminobutyric acid, ornithine and lysine. Lysine exhibits a particularly preferred coating effect, that is, surface-slipping characteristics.

The long chain acyl group preferably has from 6 to 22 carbon atoms and includes, for example, acyl groups derived from caproic acid, enanthic acid, caprylic acid, pelargonic acid, capric acid, lauric acid, myristic acid, palmitic acid, stearic acid, icosanoic acid, docosanoic acid, oleic acid, behenic acid, isostearic acid, coconut oil fatty acid and beef tallow fatty acid. Preferred acids are saturated fatty acids such as lauric acid, myristic acid, palmitic acid and stearic acid. Lauric acid is particularly preferred.

N-Acylated basic amino acids having an acyl group of less than 6 carbon atoms are too hydrophilic and cannot exhibit good coating effects. An acyl group having more than 22 carbon atoms also cannot provide good effects.

Consequently, the N-long chain monoacylated basic amino acid for use in the invention is preferably represented by the formula (I):

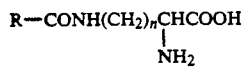

(I)

wherein R is a long chain alkyl group of from 5 to 21 carbon atoms and n is an integer of from 1 to 4. A particularly preferred compound is N-ε-lauroyl-L-lysine which has the formula (II):

(II)

The N-long chain monoacylated basic amino acid is prepared, for example, by a Shottan-Baumann reaction in which long chain carboxylic acid chloride is added dropwise to an aqueous alkali solution of basic amino acid or by a method disclosed in Japanese Patent Publication SHO 51-128610(1976) the contents of which are incorporated by reference, in which the carboxylic acid salt of the basic amino acid is dehydrated by heating.

However, no particular restriction is imposed on the method of synthesis of the N-long chain monoacylated basic amino acid and the amino acid prepared by other methods can also be used without any trouble.

The N-long chain monoacylated basic amino acid has the form of white flaky crystals having a melting point of from about 200° to about 250° C., having excellent lubricating properties, being insoluble or slightly soluble in water and common organic solvents such as chloroform and benzene, and additionally which do not swell and can be maintained in the form of a stable powder. Consequently, frictional resistance on the filament surface is effectively decreased by coating the N-long chain monoacylated basic amino acid on the filament.

Since the N-long chain monoacylated basic amino acid has good water repellency, the surgical filament surface coated with said substance sheds water effectively when the filament is exposed to body fluids or passes through wet tissue. As a result, the filament can exhibit slipping characteristics substantially equal to those in the dry state.

Further, the N-long chain monoacylated basic amino acid is extremely safe for organisms as understood from its chemical structure. When the long chain monoacyl group is a fatty acid in particular, neither acute nor subacute toxicity is found and any test results on skin irritation, mucous membrane irritation and mutagenicity are negative. Hence, it is reasonable to use said substance for the coating agent.

The surgical filament of the invention may be bioabsorbable or nonbioabsorbable and also may have a monofilament structure or an ultra fine multifilament structure. A surgical filament having a braided structure of a bioabsorbable multifilament in particular exhibits the advantageous effects of the coating of the present invention.

The material of the bioabsorbable surgical filament includes, for example, conventionally known natural substances such as catgut, collagen and chitin, and synthetic substances such as glycolide polymers (polyglycolic acid), lactide polymers (polylactic acid), glycolide-lactide copolymers, glycolide-caprolacton copolymers, polyhydroxybutyric acid, poly-p-dioxanone and trimethylene carbonate polymers.

Glycolide polymers, lactide polymers and glycolide-lactide copolymers are preferred among these polymers in view of the effect of the coating on improving the surface-slipping characteristics and filament properties such as high strength and good hydrolyzability.

Coating on the filament may be carried out by heat use of the above N-long chain monoacylated basic amino acid. For example, powder of the N-long chain monoacylated basic amino acid is directly adhered without solvent to the surface of the filament. Alternatively, the powder is suspended in a volatile solvent such as chloroform and xylene. Thereafter the filament passes through the suspension and the solvent is evaporated from the filament surface to complete coating.

The N-long chain monoacylated basic amino acid has good adhesion to the surface of the surgical filament and good coating on the filament surface can be carried out in a single step. Hence, the surface-slipping characteristics of the filament can be sufficiently improved even in a small amount.

The N-long chain monoacylated basic amino acid can be mixed with other materials and the composition thus obtained can also be coated on the filament.

Other materials to be mixed with the N-long chain monoacylated basic amino acid preferably include a polymer which is biocompatible and thermoplastic or soluble in a solvent. In particular, a polymer soluble in a solvent provides good workability in the filament coating operation and uniform coating can be achieved.

When the surgical filament is composed of a bioabsorbable polymer, the polymer to be mixed with the N-long chain monoacylated basic amino acid is preferably a bioabsorbable polymer.

The bioabsorbable polymer to be mixed includes, for example, glycolide polymers, lactide polymers, glycolide-lactide copolymers, polycaprolactone, polyoxyalkylene, polytetrafluoroethylene and silicone resins. Particularly preferred polymers are bi0absorbable polymers such as glycolide polymers, lactide polymers and glycolide-lactide copolymers.

When the N-long chain monoacylated basic amino acid is mixed with the above polymer and the resultant composition is coated on the surgical filament, the following techniques can be conducted. For example, the glycolic acid-lactic acid copolymer or polycaprolactone is heat-melted at 100° to 200° C., successively the N-long chain monoacylated basic amino acid is added, and the surgical filament passes through the molten mixture thus obtained to carry out coating. Then the coated filament is cooled in water or in air.

The preferred proportion of the N-long chain monoacylated basic amino acid in the composition is from about 30 to about 200 parts by weight per 100 parts by weight of the above polymer. When the proportion is outside of the above range, adhesion of the composition to the filament surface becomes unfavorably soft and weak.

In another method, the above polymer is dissolved in a solvent such as chloroform and dioxane at a temperature of from room temperature to about 50° C. and successively the N-long chain monoacylated basic amino acid is added to form a suspension. The surgical filament passes through the suspension to carry out coating.

The coating temperature is preferably from room temperature to about 50° C. The filament is immersed in the suspension for 5 seconds to 1 minute and can be coated satisfactorily.

The suspension is prepared by dissolving from 0.01 to 10 parts by weight of the above polymer in 100 parts by weight of the organic solvent, adding from 0.1 to 20 parts by weight of the N-long chain monoacylated basic amino acid, and maintaining the suspension at a temperature of from room temperature to about 50° C. under stirring. Stirring is continued from the preparation of the dispersion to the completion of coating in order to eliminate variations of concentration of the N-long chain monoacylated basic amino acid. After completion of the coating, the filament is dried in air for 1 to 24 hours in the temperature range of from room temperature to about 120° C. to remove the organic solvent. Drying under reduced pressure is more effective.

In the surgical filament coated with the composition consisting of a mixture of the N-long chain monoacylated basic amino acid and the above polymer, the above polymer functions as a binder for the N-long chain monoacylated basic amino acid and simultaneously stiffens the filament itself to a moderate extent. Thus the surgical filament obtained can be handled with ease. When the filament has a braided structure of a multifilament in particular, the coating can improve the disadvantage that the multifilament is too flexible and difficult to handle.

When the filament is coated with the composition composed of the N-long chain monoacylated basic amino acid and the above polymer, the amount of the N-long chain monoacylated basic amino acid in the composition is preferably 20% by weight (component ratio is 1:4) or more. The amount is more preferably 50% by weight or more, most preferably 80% by weight or more. When the amount is less than 20% by weight, the good effects of coating, that is, good surface-slipping effects cannot be expected. Hence, particularly in a wet state, it becomes difficult to carry out a smooth tie-down of a knot.

In coating the filament of the invention, other conventionally known lubricants such as calcium stearate or coating agents can be used in combination with the above N-long chain monoacylated basic amino acid. Also in such case, the amount of the N-long chain monoacylated basic amino acid in the coating composition is preferably 20% by weight or more.

The amount of the N-long chain monoacylated basic amino acid which is coated directly or as a portion of the composition on the filament of the invention varies depending upon the structure of the filament, for example, the number of filaments and density of braiding or twisting. Suitable amounts are in the range of from 0.1 to 20% by weight. An amount less than 0.1% by weight does not exhibit the good effects of the coating. On the other hand, an amount exceeding 20% by weight causes the coating agent to fall off in the form of powder and is also unfavorable because of poor appearance and bad economy. The amount is more preferably in the range of from 0.5 to 10.0% by weight.

Generally, the surgical filament of the invention can be obtained by the above-described preparing process.

A more preferred process of the present invention will be illustrated hereinafter.

The characteristic of the present invention is to use the N-long chain monoacylated basic amino acid having a specific particle size.

That is, the N-long chain monoacylated basic amino acid has a volume percentage of 80% or more of particles having a size of 20 μm or less, preferably has a volume percentage of 80% or more of particles having a size of 20 μm or less and additionally has an average particle size of 7 μm or less.

The N-long chain monoacylated basic amino acid having such particle size distribution can be prepared by grinding and/Or sieving the N-long chain monoacylated basic amino acid obtained by the above process.

No particular restriction is imposed on the method for grinding the N-long chain monoacylated basic amino acid. Conventionally used mechanical-impact grinders such as a vibrating ball-mill and a hammer ball-mill or other grinders such as jet grinders which use high speed gas flow can be preferably used. The latter is preferred in particular.

No particular limitation is placed on the method for classifying the powder or fine particles which are ground as above. Preferred methods are classification using a conventional multicyclone or a combination of several standard sieves specified in JIS Z-8801 which corresponds to ASTM E-11.

When a particle size distribution to meet the object of the invention, that is, a volume percentage of 80% or more on particles having a size of 20 μm or less cannot be obtained by grinding and classification in any of the above methods, grinding and classification are repeated to obtain particles having a suitable size distribution for the object.

In the present invention, the N-long chain monoacylated basic amino acid having the above particle size distribution (hereinafter referred to as N-long chain monoacylated basic amino acid) is applied to the surface of the surgical filament intact or in the form of a composition with other materials.

The present invention is characterized by the particle size distribution of the coating material used. No particular restriction is imposed upon the coating method applied. Exemplary methods which are preferably used include:

(1) a method for directly coating the powder or fine particles of the N-long chain monoacylated basic amino acid on the surface of the surgical filament, (2) a method for dispersing the powder or fine particles of the N-long chain monoacylated basic amino acid in water or an organic solvent and coating the resulting suspension on the filament, and (3) a method for dispersing the powder or fine particles of the N-long chain monoacylated basic amino acid in a hot melt or solution of a bioabsorbable polymer and coating the resulting suspension on the filament.

Alternatively, it is possible to dissolve the powder or fine particles of the N-long chain monoacylated basic amino acid or a composition containing the amino acid in a suitable organic solvent and coating the resulting solution on the filament. The particles of the amino acid used are relatively small in size and can be dissolved in the organic solvent with relative ease. However, the effect of solubility is not so remarkable and the solution method is not so suitable for the invention.

In the above method (1), the powder or fine particles of the N-long chain monoacylated basic amino acid is directly coated on the surface of the surgical filament at or in the vicinity of the room temperature with a finger or a brush.

Other methods which can be exemplified include a so-called spray coating method, i.e., a method for spraying the powder of the amino acid on the surface of the filament by using a stream of air, nitrogen or other inert gases which are blown under the pressure of 0.5 to 5 atmospheres at or in the vicinity of room temperature.

As an example of the above method (2), the powder or fine particles of the N-long chain monoacylated basic amino acid are dispersed at or in the vicinity of the room temperature in water or an organic solvent such as chloroform, dioxane, toluene, xylene, methanol and ethanol, and the filament is coated by passing through the resulting suspension with stirring, followed by evaporating the solvent. Other methods include, for example, a spray coating method, i.e., a method for spraying the resulting suspension by using a stream of air, nitrogen or other inert gases which are blown under the pressure of 0.5 to 5 atmospheres.

The concentration of the suspension is preferably in the range of 2 to 100 parts by weight of the coating material per 100 parts by weight of the suspending medium such as water. A concentration less than 2 parts by weight leads to an insufficient amount of the coating material adhered. On the other hand, a concentration exceeding 100 parts by weight causes unfavorable precipitation of the coating material and thus it becomes difficult to obtain a good suspension.

In the preparation of the above suspension, a small amount of a surface active agent or emulsifier can also be added in order to stabilize the suspension.

The evaporation temperature of the solvent used for dispersing the coating material, that is, the drying temperature of the filament depends upon the volatility and boiling point of the solvent used. For example, in the case of using toluene as a suspending medium, a preferred temperature is in the range of 40° to 120° C. in an inert gas such as the air or nitrogen.

Batch and continuous dryers can be used. It is important to maintain inside and outlet temperatures of the dryers above the dewpoint of the suspending medium such as toluene.

As an embodiment of the above method (3), the powder or fine particles of the N-long chain monoacylated basic amino acid is dispersed in a hot melt of a biocompatible polymer or a bioabsorbable polymer, and the surgical filament is coated by passing through the resulting dispersion and cooled. Alternatively, the biocompatible polymer or the bioabsorbable polymer is dissolved in an organic solvent such as toluene, xylene, chloroform and dioxane, the powder or fine particles of the N-long chain monoacylated basic amino acid are dispersed in the resulting solution, the surgical filament is passed through the resulting suspension or spray coated with the resulting suspension under pressure of 0.5 to 5 atmospheres, and the thus-coated filament is dried.

The polymers used in the above method preferably have biocompatibility, bioabsorbability and thermoplastic properties in use as the surgical filament.

The polymers which can be used include, for example, glycolide polymer, lactide polymer, glycolide-lactide copolymer, polycaprolactone, polyoxyalkylene, polytetrafluoroethylene and silicone resin. Particularly preferred polymers are bioabsorbable polymers such as glycolide polymer, lactide polymer and glycolide-lactide copolymer.

When a hot melt of glycolide-lactide copolymer or polycaprolactone is used, the polymer is heat-melted at 100° to 200° C., successively the N-long chain monoacylated basic amino acid is added, and the surgical filament is passed through the molten mixture thus obtained to carry out coating. Then the coated filament is cooled in water or in the air. The preferred proportion of the N-long chain monoacylated basic amino acid in the composition is from 30 to 200 parts by weight per 100 parts by weight of the above polymer. When the proportion is outside of the above range, adhesion of the composition to the filament surface becomes unfavorably soft and weak.

In another method, the above polymer is dissolved in a solvent such as toluene, xylene, chloroform and dioxane in the range of room temperature to 100° C. and successively the N-long chain monoacylated basic amino acid is added to form a suspension.

The surgical filament is passed through the suspension or sprayed by the suspension under the pressure of 0.5 to 5 atmospheres to carry out coating and successively dried.

The coating temperature is preferably from room temperature to 50° C. Higher temperature is unfavorable because solvent evaporation causes time dependent variations of concentration. Immersion of the filament in the suspension for 2 seconds to one minute can provide satisfactory coating.

The suspension is prepared by dissolving from 0.01 to 10 parts by weight of the above polymer in 100 parts by weight of the organic solvent, adding from 0.1 to 20 parts by weight of the N-long chain monoacylated basic amino acid, and maintaining at room temperature to 50° C. under stirring. Stirring is continued from the preparation of the dispersion to the completion of coating in order to eliminate variation of concentration of the N-long chain monoacylated basic amino acid. After completion of the coating, the filament is dried in air or inert gas such as nitrogen for 1 to 24 hours in the range of from room temperature to 120° C. to remove the organic solvent. Drying under reduced pressure is more effective.

Other conventionally known lubricants or coating additives can be used in combination with the N-long chain monoacylated basic amino acid in coating the filament of the invention. Exemplary lubricants and coating additives include calcium stearate, magnesium stearate, barium stearate, aluminum stearate, zinc stearate, calcium palmitate, magnesium palmitate, barium palmitate, aluminum palmitate, zinc palmitate, calcium oleate, magnesium oleate, barium oleate, aluminum oleate, zinc oleate and other metal salts of fatty acids having at least 6 carbon atoms; and esters of sucrose with fatty acids having at least 6 carbon atoms.

In these simultaneous uses, the preferred ratio of the components is from 20 to 100% by weight of the N-long chain monoacylated basic amino acid to from 0 to 80% by weight of the fatty acid metal salt.

When the amount of the N-long chain monoacylated basic amino acid is less than 20% by weight or less, improvement of surface-slipping characteristics is unsatisfactory in the wet state.

Combined use of the metal salts of fatty acids having at least 6 carbon atoms or esters of sucrose with fatty acids having at least 6 carbon atoms can be carried out in the above methods (1) to (3). However, combined use can be more preferably carried out, for example, by adding the above fatty acid metal salt in an organic solvent such as xylene, refluxing for 30 to 60 minutes with stirring at the boiling point of the solvent, cooling and the mixture to 30° to 80° C. to obtain a gelated dispersion of the fatty acid metal salt in the organic solvent. The powder of the N-long chain monoacylated basic amino acid is successively dispersed with stirring, the surgical filament is passed through the resulting suspension, and the thus-coated filament is dried.

The amount of the N-long chain monoacylated basic amino acid to be coated on the surface of the filament in the invention varies depending upon the structure of the filament, for example, the number of filaments and whether the filament is braided and twisted, and is suitably selected in the range of from 0.1 to 10% by weight for the weight of the filament.

When the amount is less than 0.1% by weight, development of a good coating effect is difficult to realize. An amount exceeding 10% by weight unfavorably leads to high cost. A more preferred amount is in the range of from 0.5 to 5.0% by weight.

The characteristic of the process is to use the N-long chain monoacylated basic amino acid of the invention having a specific particle size and relatively small particles. Hence the particles of the N-long chain monoacylated basic amino acid penetrate in good order into the gaps among multifilaments and can provide uniform coating over the whole surface of the filament.

Consequently, good slipping characteristics can be exhibited even with a small amount of coating, and appearance of the surgical filament is not impaired.

Further, the particles of N-long chain monoacylated basic amino acid seldom fall off from the surface of coated filaments during packaging, transportation, storage and use.

The present invention will hereinafter be illustrated further in detail by way of examples. Physical properties in the examples were measured by the following methods.

Tie down test

(1) Subjective method

As to the surgical filament provided by the invention, evaluation of slipping characteristics, particularly tie down property of a knot, can be carried out with extreme ease in a subjective method.

As illustrated in FIG. 1, a filament 2 which was passed under a bar 1 was firmly tied at the upper parts and then the resulting knot 3 was pulled down by drawing both ends 2a and 2b of the filament in the directions of the arrows, respectively. The slipping property could be readily evaluated by the ease of pull down.

Tie down property was classified into five grades according to the following standards for evaluation.

O: Knot does not slide at all or filament is broken.
1: Knot moves only slightly. Considerable force is required for moving the knot.
2: Knot moves with intermittent hang up.
3: Knot slides down with ease.
4: Knot slides down very smoothly.

(2) Objective method

As illustrated in FIG. 2, a filament to be tested was turned once around a cylindrical sponge 4 having an inside diameter of 40 mm and an outside diameter of 50 mm and a knot 3 was made as illustrated in FIG. 1. Both ends of the filament 2 were respectively fixed to chucks 5a and 5b of a tensile testing machine and drawn at a rate of 100 mm/min. The knot did not slide in some of the filaments 2 and the filament 2 was broken. When the knot could slide, the knot was subjected to slide a distance of 30 cm. The stress detected by a load cell 6 varied depending upon the slide distance of the filament 2. Hence, the initial 10 cm and final 10 cm were omitted from the total slide distance of 30 cm, and maximum and minimum stresses were recorded on the intermediate 10 cm.

Grinding of N-lauroyl lysine and measurement of its particle size distribution Marketed N-lauroyl lysine was ground using a single track jet mill, Model STD-4 (Trademark of Seishin Kigyo Co.), and recovered with a polyester bag filter.

N-lauroyl lysine having two kinds of particle size distribution was obtained by grinding and individually referred to as sample 11 and sample 12 of the coating material. Unground N-lauroyl lysine was referred to as sample 13.

Two or three drops of marketed liquid neutral detergent were added to 400 ml of pure water to prepare an aqueous solution containing a very small amount of surface active agent. Each 0.5 g of the above samples was added to the aqueous solution and dispersed for 3 minutes by supersonic waves.

The particle size distribution of each sample in the dispersion was measured with a light irradiation type particle size measuring instrument, Model SK-LASER MICRON SISER 7000 (Trademark of Seishin Kigyo Co.). The particle size wherein the accumulated volume percentage of particle size becomes 50 vol. % in each sample was defined as an average particle size. Table 3 illustrates the particle size distribution and average particle size of each sample.

EXAMPLES 1–10 AND COMPARATIVE EXAMPLES 1–5

Various coating agents illustrated in Table 1 in powder form were directly adhered to the filament (a kind and size of the filament are shown in Table 1) with a human finger and excess coating agent was wiped off by rubbing the filament with a dry cloth. According to the number of wiping cycles with the cloth, filaments having various amounts of the coating agents were obtained. The weights of the filaments thus obtained were measured. The adhered amounts of the coating agents were calculated from the difference in weight between the coated and original filaments, and indicated by percentage of the weight of filament.

Tie down tests were carried out on the coated and uncoated filaments as such and slipping characteristics in the dry state were evaluated by the objective method.

Filaments were immersed in distilled water at 37° C. for a minute and tie down tests were carried out to evaluate slipping characteristics by the objective method.

Results are illustrated in Table 1.

EXAMPLES 11–27 AND COMPARATIVE EXAMPLES 6–10

As illustrated in Table 2, solutions of coating agent mixtures were prepared by dissolving 1 g of various resins in the prescribed amount of chloroform and adding N-lauroyl lysine powder in the ratios illustrated in Table 1.

Subsequently, said solutions were stirred to disperse the powder and the same filaments as those used in Example 1 were immersed for about 10 seconds. The filaments were taken out and dried in the air to remove the solvent. Thus, coated filaments were obtained.

The weights of the coated filaments were measured, and the adhered amount of the coating agents were calculated from the difference of weight between the coated and original filaments. The amount was indicated by wt % of the weight of the filament.

Tie down tests were carried out by the subjective method both in the dry and wet states. Results are illustrated in Table 2.

EXAMPLE 28

A dispersion was prepared by adding 1 g of N-lauroyl lysine powder to 10 ml of xylene and stirring vigorously. The same filament as that used in Example 1 was immersed for 30 seconds in the dispersion thus obtained and then taken out and dried in the air to remove the solvent. Excess coating agent was wiped off with a dry cloth. The calculated amount of adhered coating agent was about 3.9%

Slipping characteristics were evaluated on the coated filament by the same procedures as described in Examples 11-27. The knot smoothly slid down both in the dry and wet states.

TABLE 1

| Filament | | Coating agent | (wt %) | Slipping characteristic (kgf) Dry | Wet |
|---|---|---|---|---|---|
| | (size) | | | | |
| Example 1 | PGA (2-0) | N-lauroyl lysine | 7.1 | 0.1–0.3 | 0.2–0.3 |
| Example 2 | PGA (3-0) | N-lauroyl lysine | 12.1 | 0.1–0.2 | 0.1–0.2 |
| Example 3 | PGA (2-0) | N-lauroyl lysine | 3.8 | 0.2–0.3 | 0.3–0.4 |
| Example 4 | PGA (2-0) | N-lauroyl lysine | 0.5 | 0.4–0.9 | 0.5–1.1 |
| Example 5 | PGA (2-0) | N-lauroyl lysine + Ca-stearate (5/5) | 6.5 | 0.1–0.4 | 0.3–0.5 |
| Example 6 | PGA (2-0) | N-stearoyl ornithine | 8.3 | 0.2–0.4 | 0.2–0.4 |
| Example 7 | PGA (2-0) | N-enanthoyl lysine | 9.0 | 0.3–0.5 | 0.4–0.9 |
| Example 8 | PGLA 9 (2-0) | N-lauroyl lysine | 8.2 | 0.1–0.2 | 0.2–0.3 |
| Example 9 | PLA (2-0) | N-lauroyl lysine | 6.9 | 0.1–0.3 | 0.2–0.3 |
| Example 10 | Silk yarn (2-0) | N-lauroyl lysine | 5.6 | 0.2–0.4 | 0.2–0.5 |
| Comp. Ex. 1 | PGA (2-0) | — | — | X** | X |
| Comp. Ex. 2 | PGA (2-0) | Ca-stearate | 6.9 | 0.2–0.4 | 0.9–1.2 |
| Comp. Ex. 3 | PGLA 9 (2-0) | — | — | X | X |
| Comp. Ex. 4 | PLA (2-0) | — | — | X | X |
| Comp. Ex. 5 | Silk yarn (2-0) | — | — | X | X |

Note: *Abbreviations in the filament column are as follows:
PGA: Polyglycolide multifilament suture (braided, dyed)
PLA: Polylactide multifilament suture (braided)
PGLA 9: Glycolide-lactide copolymer suture (copolymerized ratio = 9/1, braided)
Filament size: In accordance with United States Pharmacopoeia (U.S.P.)
**In the slipping characteristic column: X: Knot did not slide. Filament was broken.

TABLE 2

| | Coating agent (g) | | | Chloroform (ml) | Coating agent adhered (wt %) | Tie down evaluation | |
|---|---|---|---|---|---|---|---|
| | N-Lauroyl lysine (A) | Resin* component (B) | (A)/(B) | | | Dry | Wet |
| Example 11 | 0.25 | PLA 1.00 | 1/4 | 10 | 29.5 | 3 | 2 |
| Example 12 | 0.25 | PLA 1.00 | 1/4 | 20 | 9.8 | 3 | 2 |
| Example 13 | 1.00 | PLA 1.00 | 1/1 | 20 | 15.5 | 4 | 4 |
| Example 14 | 1.00 | PLA 1.00 | 1/1 | 40 | 3.6 | 3 | 2 |
| Example 15 | 2.00 | PLA 1.00 | 2/1 | 20 | 18.7 | 4 | 4 |
| Example 16 | 2.00 | PLA 1.00 | 2/1 | 40 | 5.2 | 3 | 3 |
| Example 17 | 4.00 | PLA 1.00 | 4/1 | 20 | 23.1 | 4 | 4 |
| Example 18 | 4.00 | PLA 1.00 | 4/1 | 40 | 9.2 | 4 | 4 |
| Example 19 | 4.00 | PLA 1.00 | 4/1 | 60 | 3.5 | 4 | 4 |
| Example 20 | 8.00 | PLA 1.00 | 8/1 | 40 | 14.9 | 4 | 4 |
| Example 21 | 8.00 | PLA 1.00 | 8/1 | 60 | 4.1 | 4 | 4 |
| Example 22 | 10.00 | PLA 1.00 | 10/1 | 40 | 16.2 | 4 | 4 |
| Example 23 | 10.00 | PLA 1.00 | 10/1 | 60 | 4.5 | 4 | 4 |
| Example 24 | 12.00 | PLA 1.00 | 12/1 | 60 | 4.3 | 4 | 4 |
| Example 25 | 4.00 | PCL 1.00 | 4/1 | 40 | 8.5 | 4 | 4 |
| Example 26 | 8.00 | PGLA5 1.00 | 8/1 | 60 | 4.9 | 4 | 4 |
| Example 27 | 1.00 | — 0 | 1/1 | 20 | 3.6 | 4 | 4 |
| Comp. Ex. 6 | 0.125 | PLA 1.00 | 1/8 | 20 | 8.9 | 2 | 1 |
| Comp. Ex. 7 | 0.125 | PLA 1.00 | 1/8 | 10 | 33.8 | 0 | 0 |
| Comp. Ex. 8 | 0 | PLA 1.00 | 0/1 | 10 | 32.5 | 0 | 0 |
| Comp. Ex. 9 | 0 | PCL 1.00 | 0/1 | 20 | 7.1 | 0 | 0 |
| Comp. Ex. 10 | 0 | PGLA5 1.00 | 0/1 | 20 | 7.9 | 0 | 0 |

Note: *Abbreviations in resin component column are as follows:
PLA: Polylactide
PCL: Polycaprolactone
PGLA5: Glycolide-lactide copolymer (copolymerized ratio = 5/5)

EXAMPLES 29-32 AND COMPARATIVE EXAMPLES 11-14

All surgical filaments used had a multifilaments braided structure. Their sizes are illustrated in Table 4 based on the specification of United States Pharmacopeia XIX (hereinafter referred to as USP).

The powder of sample 1, sample 2 or sample 3 of the coating material having various particle sizes which are illustrated in Table 3 was directly adhered to a surgical filament with a human finger and excess coating material was wiped off by rubbing the filament with a dry cloth. According to the number of wiping cycles by the cloth, filaments having various amounts of the coating agents adhered were obtained.

The weight of the filaments thus obtained was measured. The adhered amount of the coating material was calculated from the difference in weight between the coated and original filaments, and indicated by percentage of the weight of filament.

Slipping characteristics of coated filaments in the dry state were evaluated by the objective method.

Coated filaments were immersed in distilled water at 37° C. for a minute and slipping characteristics in the wet state were evaluated by the objective method as above.

The filaments coated with sample 29 and sample 30, respectively, had good slipping characteristics in spite of a small amount of coating. No falling off of the coating material was observed. Results are illustrated in Table 4.

As clearly seen in Table 4, Example 29 and Comparative Example 12, Example 30 and Comparative Example 13, and Example 32 and Comparative Example 14 are individually almost equal in the amount of the coating material adhered. In any case, the Examples had better slipping characteristics of filament surface than the Comparative Examples. The effect of specifying the particle size of the coating material could be observed. Comparative Example 14 had great absolute values of surface slipping characteristics and additionality had a large difference between maximum and minimum values.

In all Examples, no fall off of the coating material was observed in the tie down procedures and appearance of the coated filaments was good.

EXAMPLES 33-35 AND COMPARATIVE EXAMPLES 15-17

Chloroform solutions of resin were prepared by adding 1 g of the resin illustrated in Table 5 to a prescribed amount of chloroform and successively stirring at room temperature for 30 minutes.

Suspensions of the coating material were successively prepared by adding the prescribed amounts of sample 1 or sample 3 of the coating material having various particle sizes illustrated in Table 3 to the above-obtained solution with stirring.

The same filaments as used in Example 29 were immersed in the above suspensions for about 10 seconds to coat various resins and samples. Successively, the filaments were dried in the air at 50° C. for an hour to obtain coated filaments.

The adhered amount of the coating material to the filament is indicated by the total amount of the above resin and sample 1 or sample 3.

The tie down property of the filament at the wet and dry states were evaluated by the subjective method. Examples 33, 34 and 35 had better surface tie down property than Comparative Examples 15, 16 and 17, respectively, in spite of less amount of coating. All examples which used sample 1 of the coating material caused no fall off of the coating material in the tie down procedures. Further, the coated filament had good appearance. Results are illustrated in Table 5.

EXAMPLE 36

A xylene solution of poly-D,L-lactic acid having an average molecular weight of 5000 was prepared by adding 2 g of the resin to 94 g of xylene and stirring for 30 minutes at room temperature.

Successively, a suspension of the coating material was prepared by adding 4 g of sample 1 illustrated in Table 3 to the xylene solution with stirring.

The resin and sample 1 were coated on the same kind of a filament as used in Example 29 by immersing the filament in the suspension with stirring. The coated filament was dried by a hot air stream at 50° C. for an hour.

The adhered amount of the coating material was 2.3% by weight. Surface slipping characteristic of the coated filament was evaluated by the subjective method as carried out in Example 29. As a result, evaluation was grade 4. The coated filament had good appearance. No fall off of the coating material was observed in the tie down test.

EXAMPLE 37

A suspension of the coating material illustrated in Table 3 was prepared by adding 80 g of sample 1 to 1000 ml of xylene and stirring vigorously.

The suspension was sprayed on the same kind of filament as used in Example 29 at the pressure of 3 kg/cm$^2$ with a marketed manual atomizer having a content of 1000 ml and a nozzle diameter of 2 mm. The coated filament was dried in the air at 100° C. for 30 minutes.

The procedures of coating and drying were repeated three times to obtain a filament having 6.5% by weight of coated material for the weight of the filament.

The tie down property of the coated filament was evaluated by the subjective method as carried out in Example 29.

As a result, the surface slipping characteristic was grade 4 in both wet and dry states. Thus the slipping characteristic was good. No fall off of the coating material was observed in the procedures for making a knot and tying down. The coated filament had good appearance.

EXAMPLE 38

A gel dispersion was prepared by adding 40 g of calcium stearate to 1000 ml of xylene, refluxing at 150° C. for 30 minutes with stirring, and cooling to 50° C.

A suspension of the coating material illustrated in Table 3 was prepared by adding 40 g of sample 1 to the gel dispersion obtained above and stirring vigorously.

The same coating procedures as described in Example 36 were carried out except that the suspension obtained above was used. A filament having 5.8% by weight of coated material was obtained and evaluated by the same method as described in Example 37.

As a result, the surface slipping characteristic was grade 4 in both wet and dry states. Thus the slipping characteristic was good. No fall off of the coating material was observed in the procedures for making a knot and tying down. The coated filament had good appearance.

TABLE 3

| Particle size (μm) | Accumulated volume distribution of particle size (Vol. %) | | |
|---|---|---|---|
| | Sample 1 | Sample 2 | Sample 3 |
| 0.1 | 0.0 | 0.0 | 0.0 |
| 0.2 | 0.0 | 0.0 | 0.0 |
| 0.4 | 0.9 | 0.3 | 0.1 |
| 0.6 | 3.1 | 0.7 | 0.2 |
| 0.8 | 7.5 | 1.2 | 0.3 |
| 1.0 | 14.9 | 1.9 | 0.4 |
| 1.5 | 26.9 | 3.5 | 0.7 |
| 2.0 | 47.3 | 8.5 | 1.8 |
| 3.0 | 71.4 | 16.9 | 4.4 |
| 4.0 | 88.2 | 29.4 | 6.5 |
| 6.0 | 97.9 | 46.8 | 8.5 |
| 8.0 | 97.9 | 62.5 | 11.8 |
| 12.0 | 97.9 | 79.9 | 17.4 |

TABLE 3-continued

| Particle size (μm) | Accumulated volume distribution of particle size (Vol. %) | | |
|---|---|---|---|
| | Sample 1 | Sample 2 | Sample 3 |
| 16.0 | 97.9 | 89.1 | 28.7 |
| 24.0 | 97.9 | 96.8 | 54.0 |
| 32.0 | 100.0 | 100.0 | 72.2 |
| 48.0 | 100.0 | 100.0 | 91.9 |
| 64.0 | 100.0 | 100.0 | 97.0 |
| 96.0 | 100.0 | 100.0 | 99.4 |
| 128.0 | 100.0 | 100.0 | 100.0 |
| 192.0 | 100.0 | 100.0 | 100.0 |
| Average particle size (μm) | 2.1 | 6.4 | 22.7 |

TABLE 4

| | Example | | | | Comparative Example | | | |
|---|---|---|---|---|---|---|---|---|
| | 29 | 30 | 31 | 32 | 11 | 12 | 13 | 14 |
| Kind of filament* | 2-0 | 2-0 | 3-0 | 2 | 2-0 | 2-0 | 2-0 | 2 |
| Sample No. | 1 | 1 | 2 | 1 | 3 | 3 | 3 | 3 |
| Adhered amount (wt %) | 3.7 | 1.9 | 2.9 | 0.6 | 7.1 | 3.8 | 2.0 | 0.5 |
| Slipping characteristics | | | | | | | | |
| Dry (Kgf) | 0.1~0.2 | 0.1~0.2 | 0.1~0.2 | 0.2~0.4 | 0.1~0.3 | 0.2~0.3 | 0.3~0.4 | 0.4~0.9 |
| Wet (Kgf) | 0.1~0.2 | 0.1~0.3 | 0.2~0.3 | 0.3~0.5 | 0.2~0.3 | 0.3~0.4 | 0.4~0.6 | 0.5~1.1 |
| Appearance | good | good | good | good | white | white | pale white | good |
| Fall off in tie down | no | no | no | no | violent | found | found | no |

Note: *Polyglycolide filament
Size is indicated according to USPXIX specification.

TABLE 5

| | Example | | | Comparative Example | | |
|---|---|---|---|---|---|---|
| | 33 | 34 | 35 | 14 | 15 | 16 |
| Kind of filament* | 2-0 | 2-0 | 2-0 | 2-0 | 2-0 | 2-0 |
| Chloroform (ml) | 40 | 40 | 70 | 40 | 40 | 70 |
| Coating resin (g)** | 1.0 | 1.0 | 1.0 | 1.0 | 1.0 | 1.0 |
| Sample No. | 1 | 1 | 1 | 3 | 3 | 3 |
| N-Lauroyl lysine (g) | 1.0 | 2.0 | 4.0 | 1.0 | 2.0 | 4.0 |
| Adhered amount (wt %) | 3.2 | 4.3 | 1.9 | 3.6 | 5.2 | 2.0 |
| Tie down | | | | | | |
| Dry | 4 | 4 | 3 | 3 | 3 | 2 |
| Wet | 3 | 4 | 3 | 2 | 3 | 1 |
| Appearance | good | good | good | pale white | white | pale white |
| Fall off in tie down | no | no | no | found | found | no |

Note: *Polyglycolide. Size is illustrated according to USP XIX specification.
**Poly-L-lactide
***Tie down property was classified into five grades according to the following standards for evaluation.
0: Knot does not slide at all or filament is broken.
1: Knot moves only slightly. Considerable force is required for moving the knot.
2: Knot moves with intermittent hang up.
3: Knot can be slid down with ease.
4: Knot slides down very smoothly.

What is claimed is:

1. A surgical filament comprising a surface coated with at least one N-long chain monoacylated basic amino acid which has an aliphatic acyl group of from 6 to 22 carbon atoms.

2. The surgical filament of claim 1 wherein the surgical filament is a bioabsorbable polymer.

3. The surgical filament of claim 2 wherein the bioabsorbable polymer is a polymer of at least one of glycolide and lactide.

4. The surgical filament of claim 1 wherein said N-long chain monoacylated basic amino acid which has an aliphatic acyl group of from 6 to 22 carbon atoms is a compound represented by the formula (I):

$$R-CONH(CH_2)_n\underset{NH_2}{CHCOOH} \quad (I)$$

wherein R is a long chain alkyl group having from 5 to 21 carbon atoms, and n is an integer of from 1 to 4.

5. The surgical filament of claim 4 wherein R is an undecyl group and n is 4 in the formula (I).

6. The surgical filament of claim 1 wherein the amount of the N-long chain monoacylated basic amino acid which has an aliphatic acyl group of from 6 to 22 carbon atoms is from 0.1 to 20 parts by weight per 100 parts by weight of the filament.

7. A surgical filament comprising a surface coated with a composition containing at least one N-long chain monoacylated basic amino acid which as an aliphatic acyl group of from 6 to 22 carbon atoms and a bioabsorbable polymer.

8. The surgical filament of claim 7 wherein the surgical filament is a bioabsorbable polymer.

9. The surgical filament of claim 8 wherein the bioabsorbable polymer is a polymer of at least one of glycolide and lactide.

10. The surgical filament of claim 7 wherein said N-long chain monoacylated basic amino acid which has an aliphatic acyl group of from 6 to 22 carbon atoms is a compound represented by the formula (I):

$$R-CONH(CH_2)_n\underset{NH_2}{CHCOOH} \quad (I)$$

wherein R is a long chain alkyl group having from 5 to 21 carbon atoms, and n is an integer of from 1 to 4.

11. The surgical filament of claim 10 wherein R is an undecyl group and n is 4 in the formula (I).

12. The surgical filament of claim 7 wherein the amount of the N-long chain monoacylated basic amino acid which has an aliphatic acyl group of from 6 to 22 carbon atoms is from 0.1 to 20 parts by weight per 100 parts by weight of the filament.

* * * * *